(12) United States Patent
Guerra

(10) Patent No.: US 6,649,857 B1
(45) Date of Patent: Nov. 18, 2003

(54) NEEDLE DESTRUCTION DEVICE

(75) Inventor: Lawrence E. Guerra, Shawnee, KS (US)

(73) Assignee: Pointe-Safe, L.L.C., Lenexa, KS (US)

( * ) Notice: Subject to any disclaimer, the term of this patent is extended or adjusted under 35 U.S.C. 154(b) by 0 days.

(21) Appl. No.: 10/192,358

(22) Filed: Jul. 10, 2002

(51) Int. Cl.[7] .............................................. B23H 1/00
(52) U.S. Cl. ..................................................... 219/68
(58) Field of Search .......................... 219/68, 69.1, 385; 83/16

(56) References Cited

U.S. PATENT DOCUMENTS

| | | |
|---|---|---|
| 4,628,169 A | 12/1986 | Ch'ing-Lung |
| 4,965,426 A * | 10/1990 | Colombo ..................... 219/68 |
| 5,091,621 A | 2/1992 | Butler |
| 5,211,628 A | 5/1993 | Marshall |
| 5,294,767 A | 3/1994 | Cantarero |
| 5,336,862 A | 8/1994 | Yelvington |
| 5,468,928 A | 11/1995 | Yelvington |
| 5,525,772 A | 6/1996 | Tanguy |
| 5,548,095 A * | 8/1996 | Cornell ........................ 219/68 |
| 5,551,355 A | 9/1996 | Haines et al. |
| 5,710,404 A | 1/1998 | Descent |
| 5,736,706 A | 4/1998 | Butler |
| 5,851,522 A | 12/1998 | Herman |
| 5,868,709 A | 2/1999 | Champion et al. |
| 5,877,469 A | 3/1999 | Truesdale et al. |
| 6,050,977 A | 4/2000 | Adams |
| 6,169,259 B1 | 1/2001 | Hall et al. |
| D440,309 S | 4/2001 | Whiteside et al. |
| 6,376,792 B1 * | 4/2002 | Cebollero et al. ............ 219/68 |

* cited by examiner

Primary Examiner—M. Alexandra Elve
(74) Attorney, Agent, or Firm—Stinson Morrison Hecker LLP

(57) ABSTRACT

A needle destruction device is provided. This device has a housing with a first electrode and a second electrode positioned therein in such a way as to create an annular space between the electrodes. In use, a needle is inserted into an opening in the housing and then into the annular space between the electrodes. This creates a short circuit, and the needle is destroyed by the high temperature resulting from the short circuit.

18 Claims, 4 Drawing Sheets

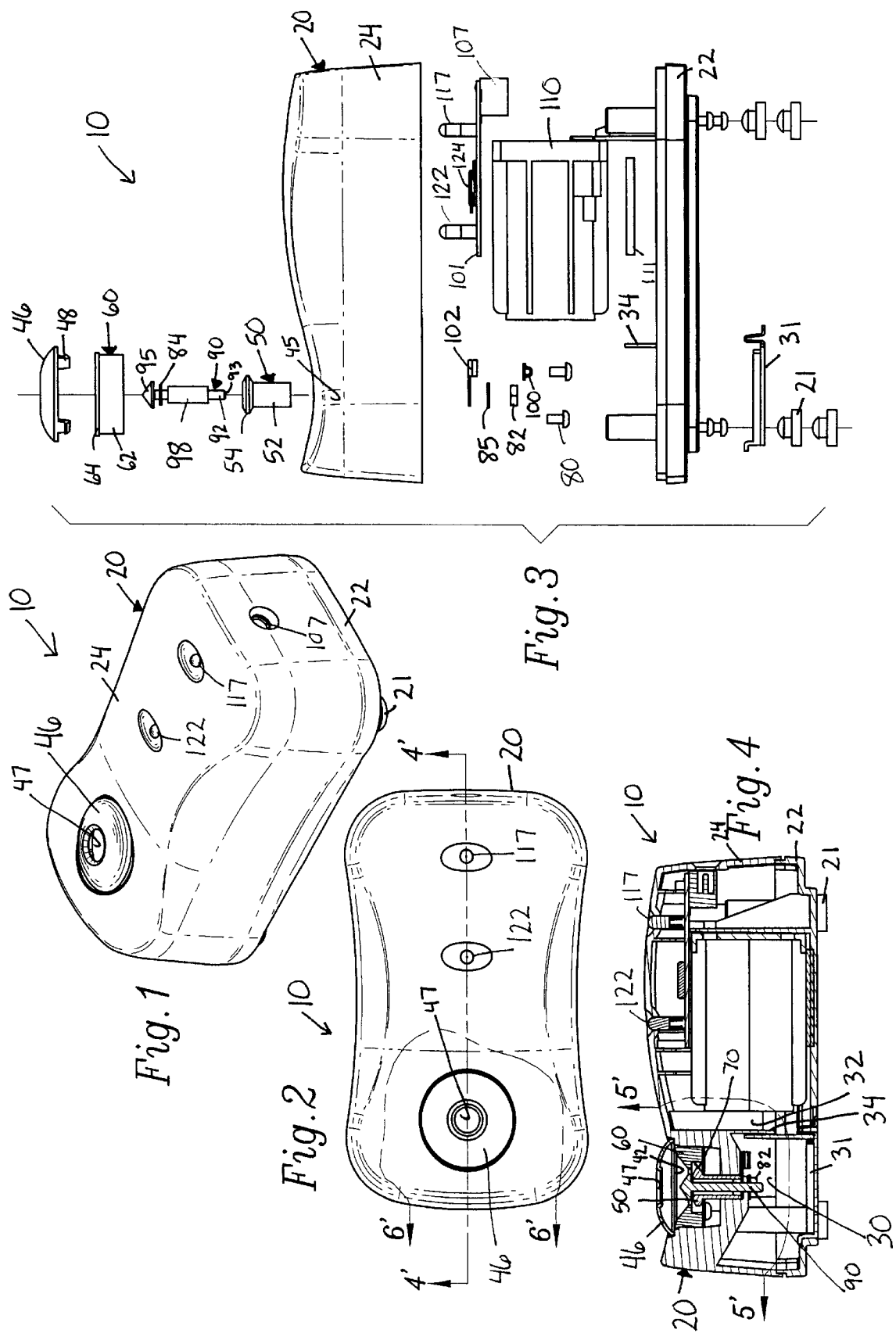

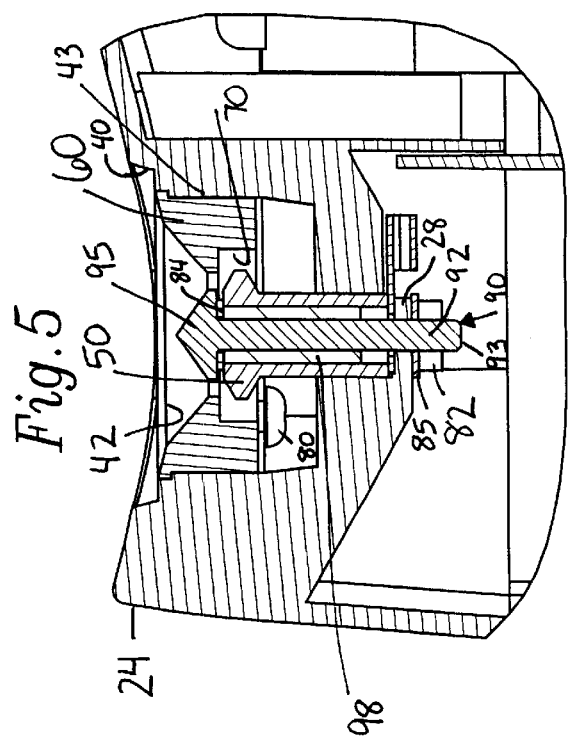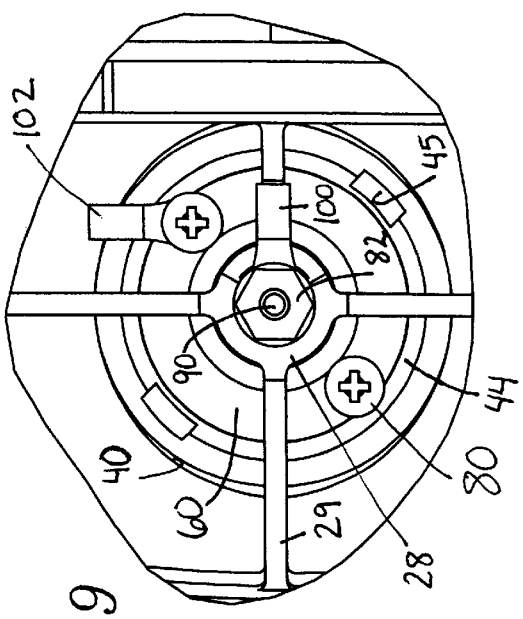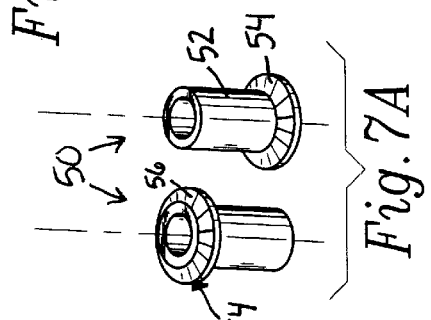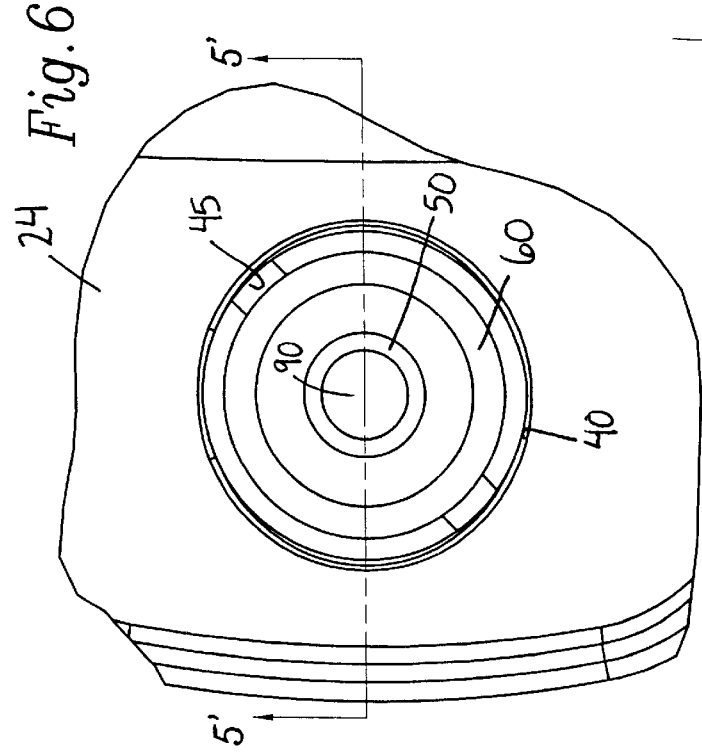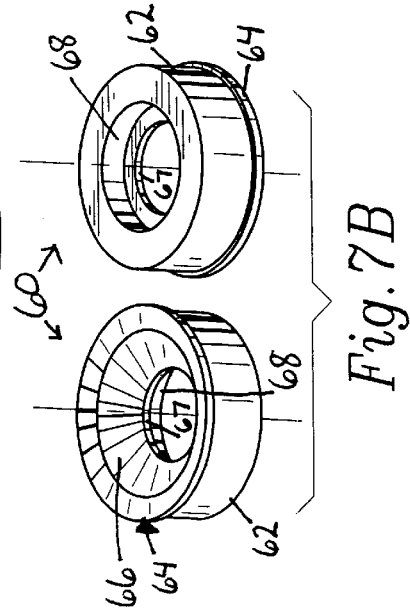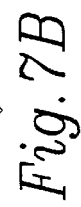

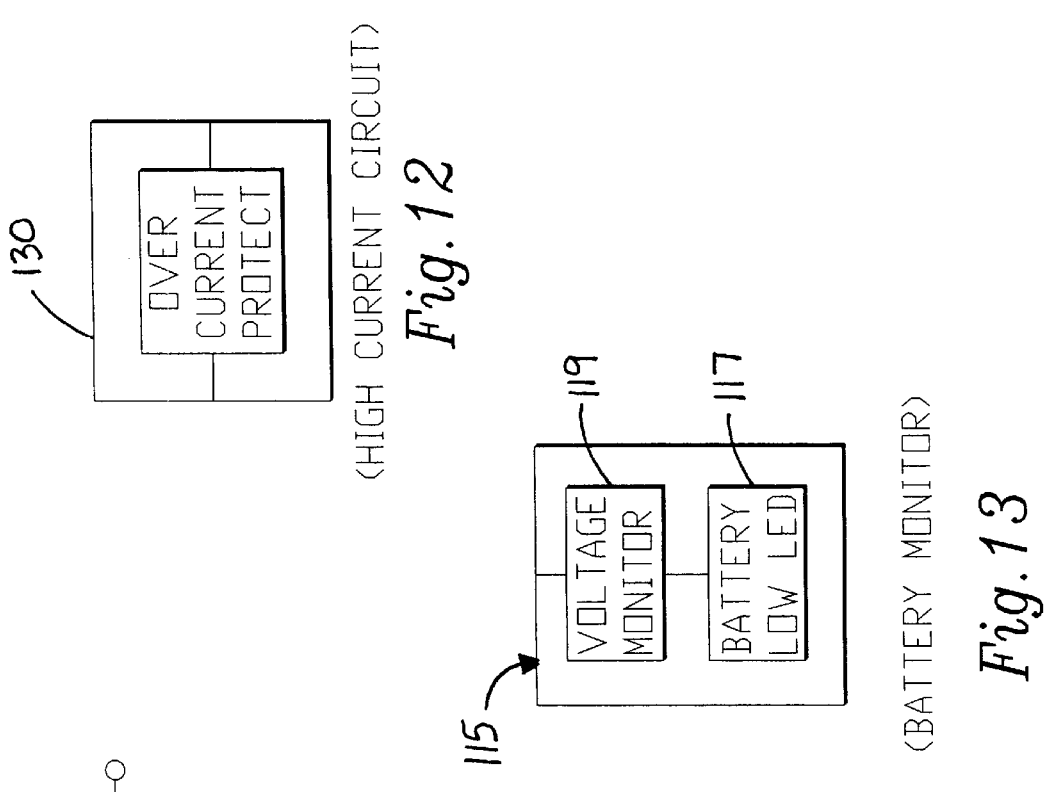
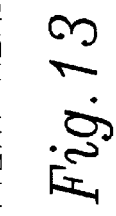
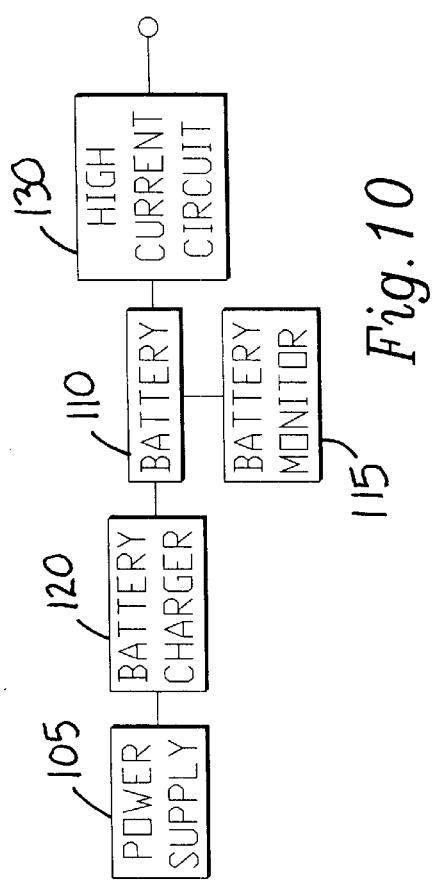
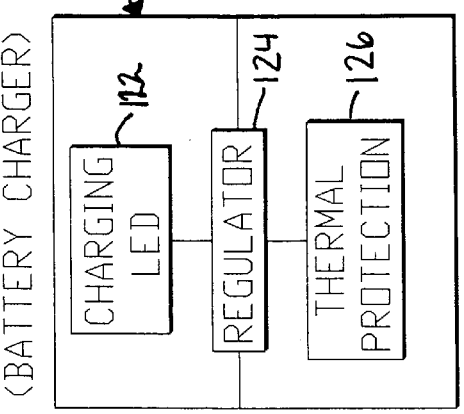

NEEDLE DESTRUCTION DEVICE

STATEMENT REGARDING FEDERALLY SPONSORED RESEARCH OR DEVELOPMENT

Not Applicable.

FIELD OF THE INVENTION

The present invention relates generally to an apparatus for disposing of needles utilized for medical purposes. More particularly, the invented apparatus is for use in destroying such needles after use.

DESCRIPTION OF RELATED ART

Medical use of needles in syringes, IV's and blood withdrawal result in the need for safe disposal of the needles after use. Blood borne pathogens, such as those associated with AIDS, can contaminate a used needle. When an injection is given, the blood of the recipient is left on the exterior of the needle and can also enter the tip of the needle, sometimes flowing all the way to the syringe, thus infecting all or part of the apparatus. Withdrawal of blood for tests and blood banks involve drawing potentially infected blood into the needle and syringe area.

In recent years, small incinerating devices have been developed that are specifically designed for destroying hypodermic syringe needles. The needles may be destroyed by inserting the metal needle, attached to the hypodermic syringe, into the incinerating apparatus where heat or electricity is utilized to thermally neutralize, melt, or disintegrate the needle. Some examples of such incinerators are found in Ch'ing-Lung, U.S. Pat. No. 4,628,169; Butler, U.S. Pat. No. 5,091,621; Cantarero, U.S. Pat. No. 5,294,767; Yelvington, U.S. Pat. No. 5,336,862; Yelvington, U.S. Pat. No. 5,468,928; Tanguy, U.S. Pat. No. 5,525,772; Haines et al., U.S. Pat. No. 5,551,355; Descent, U.S. Pat. No. 5,710,414; Butler; U.S. Pat. No. 5,736,706; Champion et al., U.S. Pat. No. 5,868,709; Truesdale et al., U.S. Pat. No. 5,877,469; Hall et al., U.S. Pat. No. 6,169,259; and Whiteside et al., U.S. Des. Pat. No. D440,309. However, in all of these devices, the user sometimes has difficulty inserting the needle into the device at the proper location and angle. Accordingly, there remains a need to provide a needle destruction apparatus that provides the user with increased flexibility in this regard.

BRIEF SUMMARY OF THE INVENTION

An object of the present invention is to provide an apparatus that is able to destroy needles using high temperatures that are generated by an electrical current so that diseases are not spread through discarded needles.

Another object of the present invention is to provide a needle destruction apparatus that is lightweight and portable.

Yet another object of the present invention is to provide an apparatus that enables the user to have increased flexibility regarding the location and angle of placement of a needle into the apparatus.

It is a further object the present to provide a needle destruction apparatus that is relatively inexpensive to manufacture and easy to assemble.

According to the present invention, the foregoing and other objects are achieved by a needle destruction device. This device has a housing with a first electrode and a second electrode positioned therein in such a way as to create an annular space between the electrodes. In use, a needle is inserted into an opening in the housing and then into the annular space between the electrodes. This creates a short circuit, and the needle is destroyed by the high temperature resulting from the short circuit.

Additional objects, advantages, and novel features of the invention will be set forth in the description that follows and in part will become apparent to those skilled in the art upon examination of the following, or may be learned by practice of the invention.

BRIEF DESCRIPTION OF THE DRAWINGS

In the accompanying drawings, which form a part of this specification, which ad in conjunction therewith and in which like reference numerals are used to parts in the various views:

FIG. 1 is a perspective view of a needle destruction apparatus in accordance sent invention;

FIG. 2 is a top plan view of the needle destruction apparatus shown in FIG. 1;

FIG. 3 is an exploded side elevational view of the needle destruction apparatus in accordance with the present invention;

FIG. 4 is a cross-sectional view of the needle destruction apparatus shown in FIG. 2 taken along line 4'—4';

FIG. 5 is an enlarged fragmentary cross-sectional view of a portion of the needle desruction apparatus taken along line 5'—5' of FIG. 4;

FIG. 6 is an enlarged fragmentary top view of a portion of the needle apparatus taken along line 6'—6' of FIG. 2 with the cover removed to show details of construction;

FIGS. 7A and 7B are top and bottom perspective views of the first electrode and the second electrode, respectively, in accordance with the present invention;

FIG. 9 is a bottom fragmentary plan view of a portion of the needle n apparatus with the door removed;

FIG. 10 is a block diagram of the electronic circuitry of the needle destruction in accordance with the present invention;

FIG. 11 is a block diagram of the battery charger component of FIG. 10;

FIG. 12 is a block diagram of the high current circuit component of FIG. 10; and FIG. 13 is a block diagram of the battery monitor component of FIG. 10.

DETAILED DESCRIPTION OF PREFERRED EMBODIMENT

Figure 8:
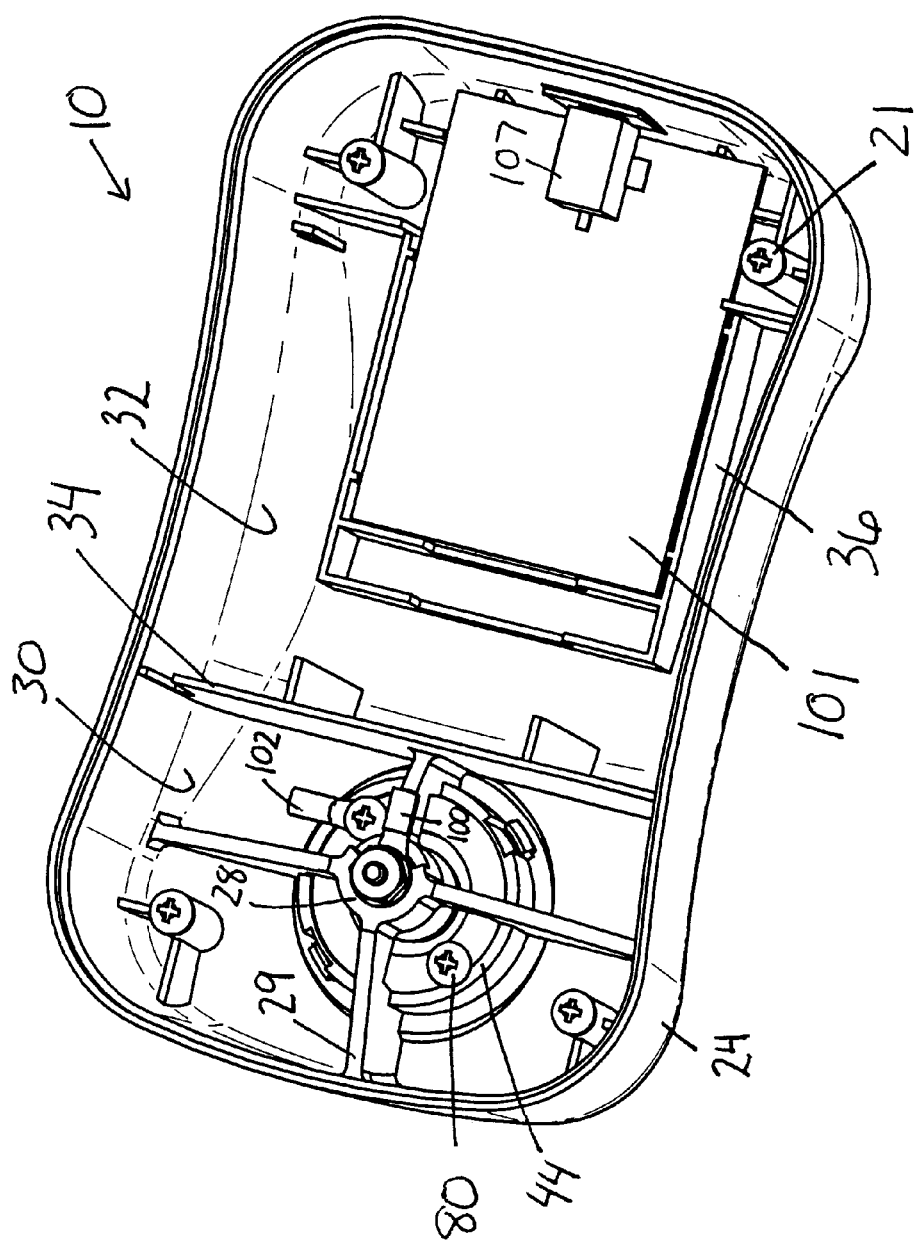
FIG. 8 is a bottom perspective view of the needle destruction apparatus with first half and the battery removed.

The present invention relates to an apparatus for destroying needles. The following description is presented to enable one of ordinary skill in the art to make and use the invention as provided in the context of a particular application and its requirements. Various modifications to the preferred embodiment will be readily apparent to those skilled in the art, and the generic principles defined here may be applied to other embodiments. Thus, the present invention is not intended to be limited to the embodiments shown, but it is to be accorded the widest scope consistent with the principles and novel features disclosed herein.

Turning now to FIGS. 1 and 2, the needle destruction apparatus of the present invention is broadly designated by reference numeral 10. The operative components of the apparatus (10) are generally hidden from view by a housing (20), which rests on a plurality (e.g. four) of feet (21). The housing (20) can be made of any suitable material know to those skilled in the art. In the present invention, the housing is preferably comprised of an injection-molded thermoplastic resin, such as acrylonitrile-butadiene-styrene ("ABS").

The housing (20) can be any suitable shape or size, and it can be comprised of one or more pieces. As shown in FIG. 3, in the preferred embodiment, the housing comprises a lower first half (22) and an upper second half (24). As discussed more fully below, the operative elements of the needle destruction apparatus (10) are mounted and positioned in the upper second half (24) of the housing (20) so as to provide for easy assembly and manufacture.

The housing (20) can form one or more compartments. The housing (20) of the preferred needle destruction apparatus has a plurality of compartments. FIGS. 4 and 8 show that, in the preferred embodiment, the housing (20) is generally divided into a first compartment (30) that contains the needle destruction area and a second compartment (32) that contains the power source of the apparatus (10). The compartments (30, 32) are separated by a compartment wall (34). As shown in FIG. 4, the compartment wall is preferably formed from a portion of the first lower half (22) of the housing (20) and from a portion of the second upper half (24) of the housing (20) so that there is a gap between each portion. As discussed more fully below, via the gap, wires (not shown) from the needle destruction area in the first compartment (30) can be connected to the power source located in the second compartment (32). Of course, those skilled in the art will recognize a hole, space, or other orifice could be used.

As shown in FIGS. 5 and 6, the upper second half (24) of the housing (20) has an opening for receiving a needle. In the preferred embodiment, a grooved recess (40) in the housing (20) leads to the opening. The opening preferably includes a cavity (42) defined by a cavity wall (43). A first electrode (50) and a second electrode (60) reside at least in part in the cavity (42) of the opening. Referring to FIGS. 1, 2 and 4, a cover (46) having a hole (47) therein preferably lies over the electrodes and is removably coupled with the housing by one or more hooks (48), which are shown in FIG. 3 and extend into corresponding slots (45) in the housing (20).

The electrodes used in the invention can be any suitable shape and size. As shown in FIG. 7A, the first electrode (50) is preferably comprised of an annular cylinder (52) coupled with a flange (54) at one end. The top surface of flange (54) of the first electrode (50) also preferably has a tapered portion (56) that extends outwardly and downwardly.

As depicted in FIG. 7B, the second electrode (60) is also preferably comprised of an annular cylinder (62) having a flange (64) at one end. The inner wall of the second electrode (60) has a tapered portion (66) that extends downwardly and inwardly, a small vertical inner edge (67), and a recessed portion (68). The first and second electrodes are comprised of any suitable conducting material and preferably are comprised of copper or a copper alloy.

When the apparatus (10) is assembled, the electrodes (50, 60) are positioned so that the flange (54) of the first electrode (50) resides just below the small vertical inner edge (67) of the second electrode (60) and at least partially within the recessed portion (68) of the second electrode (60) without touching the electrode (60), thereby creating an annular needle destruction area (70), as shown in FIG. 5. During use, the needle is placed in the annular needle destruction area (70), creating a short circuit.

As illustrated in FIGS. 4 and 5, the second electrode (60) fits snugly into the cavity (42) of the housing. The annular cylinder (62) preferably rests against the cavity wall (43). The flange (64) of the second electrode (60) rests on the grooved recess (40) of the housing (20) to prevent the second electrode (60) from falling through the cavity (42). One or more threaded holes (not shown) in the second electrode (60) are also used to secure the second electrode (60) to the lower edge (44) of the cavity wall (43), which is shown in FIG. 8, using one or more screws (80). As also shown in FIG. 8, two screws (80) are used to secure the second electrode (60) in place in the preferred embodiment.

As illustrated best in FIGS. 8 and 9, to position the first electrode (50) in the apparatus (10), the upper first half (24) of the housing (20) includes a hollow cylinder (28) positioned substantially at the center of the first compartment (30) by a plurality of centering braces (29). The hollow cylinder (28) and centering braces (29) are an integral part of the upper first half (24) of the housing. At least a portion of the annular cylinder (52) of the first electrode (50) fits inside the hollow cylinder (28) in the housing of the first compartment (30).

In order to better align the first electrode (50), as shown in FIG. 5, a retainer (90) is positioned inside the annular cylinder (52) of the first electrode (50). In the preferred embodiment, the retainer (90) has a shaft (92) and a head (95). The head (95) of the retainer (90) is positioned above the flange (52) of the first electrode (50) while the shaft (92) of the retainer (90) extends through the annular cylinder (52) of the first electrode (50) and through the hollow cylinder (28) of the first compartment (30). The shaft end (93) of the retainer (90) is preferably threaded and engages a nut (82) to secure the retainer (90) —and thus the first electrode (50) —in place.

In the preferred embodiment, as shown in FIG. 5, a sleeve (98) resides between a portion or all of the annular cylinder (52) of the first electrode (50) and the shaft (92) of the retainer (90). The sleeve can be comprised of any suitable material, but preferably it is comprised of nylon.

To position the first electrode, as further shown in FIG. 5, one or more washers (84) may reside between the head (95) of the retainer (90) and the first electrode (50). In addition, one or more washers (85) may be used between the nut (82) and the hollow cylinder (28) of the first compartment (30). The washers may be any suitable material but are preferably comprised of nylon.

As shown in FIGS. 8 and 9, the needle destruction apparatus (10) has two terminals (100, 102) that are used to connect the first and second electrodes (50, 60) to a power source, such as a battery, outlet, or other well-known device. In the preferred embodiment, as shown in FIGS. 5 and 9, the first electrode (50) is connected to a lower ring terminal (100) via a slot or aperture (not shown) in the hollow cylinder (28). A wire (not shown) leads from the lower ring terminal (100) to a printed circuit board (101) located in the second compartment (32). In the preferred embodiment, the second electrode (60) is connected to an upper ring terminal (102) using one of the screws (80) that is also used to position the second electrode (60). A wire (not shown) leads from the upper ring terminal to a battery (110) located in the second compartment (32). Foam (111) is placed in lower half (22) below battery (110).

The printed circuit board (101) is preferably is positioned in the second compartment (32) of the housing (20) using one or more support ribs (36). In the preferred embodiment, the battery is a 4-volt DC battery.

As illustrated in FIG. 10, the electronic circuitry of a preferred embodiment of the present invention includes a power supply (105), a battery charger (120), a battery (110), a battery monitor (115), and a high current circuit (130). Power supply (105) converts supply voltage to DC voltage which supplies the battery charger (120) via jack (107). As best seen in FIG. 11, battery charger (120) includes a charging LED (122) to indicate when the power supply voltage is present, a regulator (124) to regulate the DC charge voltage provided to the battery (110), and a thermal protection circuit (126), which shuts down the battery charger circuitry in the event an over-temperature condition is detected. Charging LED (122) is electrically coupled with regulator (124), which is electrically coupled with thermal protection circuit (126). Battery charger (120) supplies voltage to battery (110). Battery (110) provides voltage to the high current circuit (130), which in-turn provides current to the first electrode of the apparatus. As shown in FIG. 12, high current circuit 130 includes an over-current protection means to prevent excessive current from flowing to the electrode. A battery monitor (115) is electrically coupled with battery (110) to monitor its voltage. As seen in FIG. 13, battery monitor (115) includes a voltage monitor (119), which detects when the battery voltage is low, coupled with a battery low LED, which indicates when a low-voltage state has been detected. While not shown, it is understood that a ground reference connects the electronic circuitry, the battery, and the second of the apparatus.

In general, during use, a needle head is inserted into cavity (42) and then into the annular space (70) formed between the first and second electrodes (50, 60), creating a short circuit. The needle head is destroyed by the high temperature resulting from the short circuit. Any remaining residue from the needle falls into the first compartment (30), which has a door (31) thereon so that the residue can be easily removed.

Although the present invention has been described in accordance with the embodiments shown in the figures, one of ordinary skill in the art will recognize there could be variations to those embodiments and those variations would be within the spirit and scope of the present invention. Accordingly, many modifications may be made by one of ordinary skill in the art without departing from the spirit and scope of the present invention, the scope of which is defined by the appended claims.

I claim:

1. An apparatus for destroying needles, comprising:
   a housing having an opening for receiving a needle;
   a first electrode retained at least in part in said housing;
   a second electrode retained at least in part in said housing and positioned to create an annular space between said first electrode and said second electrode; and
   a power source electrically coupled with said first and second electrodes.

2. The apparatus of claim 1 wherein said opening in said housing includes a cavity having a cavity wall and said first electrode and said second electrode reside at least in part in said cavity.

3. The apparatus of claim 1, further comprising:
   a cover removably coupled with said housing and overlying said first and second electrodes.

4. The apparatus of claim 1 wherein said first electrode comprises a substantially annular cylinder.

5. The apparatus of claim 4 wherein said first electrode comprises a flange coupled with said cylinder.

6. The apparatus of claim 5 wherein said flange has a tapered portion.

7. The apparatus of claim 1 wherein said second electrode comprises a substantially annular cylinder.

8. The apparatus of claim 7 wherein said first electrode resides partially inside said annular cylinder of said second electrode.

9. The apparatus of claim 7 wherein said second electrode comprises a flange coupled with said cylinder.

10. The apparatus of claim 7 wherein said second electrode has an inner wall having a recessed portion.

11. The apparatus of claim 10 wherein said first electrode resides at least partially within said recessed portion of said second electrode.

12. The apparatus of claim 4, further comprising:
    a retainer comprised of a shaft and a head, wherein said shaft extends at least partially through said annular cylinder of said first electrode.

13. The apparatus of claim 12, further comprising:
    a sleeve positioned between said annular cylinder of said first electrode and said shaft of said retainer.

14. The apparatus of claim 1 wherein said power source is portable.

15. The apparatus of claim 14 wherein said power source is a battery.

16. The apparatus of claim 1 wherein said housing is comprised of at least two compartments, a first compartment for housing said electrodes and a second compartment for housing said power source.

17. A method of making an apparatus for destroying needles, comprising:
    providing a housing having an opening therein for receiving a needle;
    placing a first electrode at least partially within said housing;
    placing a second electrode at least partially in said housing;
    positioning said second electrode so as to create an annular space between said first electrode and said second electrode; and
    electrically coupling said first electrode and said second electrode to a power source.

18. A method of using a needle destruction apparatus to destroy a needle, comprising:
    providing an apparatus for destroying needles that is comprised of a housing having an opening for receiving a needle, a first electrode retained at least in part in said housing, a second electrode retained at least in part in said housing and positioned to create an annular space between said first electrode and said second electrode, and a power source electrically coupled with said first and second electrodes;
    inserting a needle into said opening of said housing and into said annular space so as to create a short circuit; and
    allowing the heat of said short circuit to destroy said needle.

* * * * *